US010327901B2

(12) United States Patent
Righini et al.

(10) Patent No.: US 10,327,901 B2
(45) Date of Patent: Jun. 25, 2019

(54) DEVICE FOR THE DEPLOYMENT OF A SYSTEM OF GUIDE WIRES WITHIN A CARDIAC CHAMBER FOR IMPLANTING A PROSTHETIC HEART VALVE

(71) Applicants: Giovanni Righini, Gland (CH); Sarah Zanon, Gland (CH)

(72) Inventors: Giovanni Righini, Gland (CH); Sarah Zanon, Gland (CH)

(73) Assignee: INNOVHEART S.R.L., Milan (IT)

(*) Notice: Subject to any disclaimer, the term of this patent is extended or adjusted under 35 U.S.C. 154(b) by 487 days.

(21) Appl. No.: 14/714,420

(22) Filed: May 18, 2015

(65) Prior Publication Data
US 2015/0245910 A1 Sep. 3, 2015

Related U.S. Application Data

(63) Continuation of application No. PCT/IB2013/060249, filed on Nov. 19, 2013, and a
(Continued)

(30) Foreign Application Priority Data

Nov. 20, 2012 (IT) .............................. B02012A0635
Nov. 20, 2012 (IT) .............................. B02012A0636

(51) Int. Cl.
*A61F 2/24* (2006.01)
(52) U.S. Cl.
CPC ............ *A61F 2/2466* (2013.01); *A61F 2/243* (2013.01); *A61F 2/2436* (2013.01); *A61F 2/2445* (2013.01); *A61F 2/2448* (2013.01)
(58) Field of Classification Search
CPC ...... A61F 2/2427; A61F 2/243; A61F 2/2436; A61F 2/2442; A61F 2/2445;
(Continued)

(56) References Cited

U.S. PATENT DOCUMENTS 7,381,219 B2 6/2008 Salahieh et al.
7,648,528 B2 1/2010 Styrc
(Continued)

FOREIGN PATENT DOCUMENTS

FR 2 874 813 A1 3/2006
WO WO 00/44311 A2 8/2000
(Continued)

OTHER PUBLICATIONS

International Search Report issued in Application No. PCT/IB2013/060249 dated May 13, 2014 (7 pages).
(Continued)

*Primary Examiner* — Robert A Lynch
(74) *Attorney, Agent, or Firm* — Flynn Thiel, P.C.

(57) ABSTRACT

A prosthetic system for heart valve replacement comprises an annular support structure within which a valved prosthetic body can be expanded until it meets opposition. The annular support is provided in ring segments having terminal connectors for forming, in the condition of use of the prosthetic system, a stable and durable annular structural continuity capable of withstanding the opposition exerted by the valved prosthetic body. The prosthetic system is deployed using guide wires within a cardiac chamber guided through an introducer catheter having through lumens, within which at least two first guide catheters are positioned. These guide catheters have respective deflected or deflectable distal ends adapted to emerge from the distal end of the introducer catheter to convey and direct the distal ends of respective guide wires, placed within the guide catheters, towards a capture member of a capture system which is provided within the introducer catheter.

19 Claims, 12 Drawing Sheets

FIG. 11a

Related U.S. Application Data continuation of application No. PCT/IB2013/060250, filed on Nov. 19, 2013.

(58) Field of Classification Search
CPC .... A61F 2/2448; A61F 2/2454; A61F 2/2457; A61F 2/2466; A61F 2/2475; A61B 17/221

See application file for complete search history.

(56) References Cited

U.S. PATENT DOCUMENTS

| | | |
|---|---|---|
| 7,927,371 B2 | 4/2011 | Navia et al. |
| 7,947,075 B2 | 5/2011 | Goetz et al. |
| 8,236,049 B2 | 8/2012 | Rowe et al. |
| 8,287,591 B2 | 10/2012 | Keidar et al. |
| 8,323,335 B2 | 12/2012 | Rowe et al. |
| 8,398,708 B2 | 3/2013 | Meiri et al. |
| 8,430,926 B2 | 4/2013 | Kirson |
| 8,444,689 B2 | 5/2013 | Zhang |
| 8,449,605 B2 | 5/2013 | Lichtenstein et al. |
| 8,597,348 B2 | 12/2013 | Rowe et al. |
| 2005/0137691 A1 | 6/2005 | Salahieh et al. |
| 2007/0233239 A1 | 10/2007 | Navia et al. |
| 2008/0004697 A1 | 1/2008 | Lichtenstein et al. |
| 2008/0077234 A1 | 3/2008 | Styrc |
| 2009/0234318 A1 | 9/2009 | Loulmet et al. |
| 2012/0123531 A1* | 5/2012 | Tsukashima .......... A61F 2/2448 623/2.37 |
| 2012/0289945 A1 | 11/2012 | Segermark |
| 2013/0116779 A1 | 5/2013 | Weber |

FOREIGN PATENT DOCUMENTS

| | | |
|---|---|---|
| WO | WO 2006/027499 A2 | 3/2006 |
| WO | WO 2006/105084 A2 | 10/2006 |
| WO | WO 2008/068756 A2 | 6/2008 |
| WO | WO 2009/002548 A1 | 12/2008 |
| WO | WO 2011/109813 A2 | 9/2011 |
| WO | WO 2012/004679 A2 | 1/2012 |
| WO | WO 2012/011108 A2 | 1/2012 |
| WO | WO 2012/063228 A1 | 5/2012 |
| WO | WO 2012/087842 A1 | 6/2012 |
| WO | WO 2013/096541 A1 | 6/2013 |

OTHER PUBLICATIONS

International Search Report issued in Application No. PCT/IB2013/060250 dated Apr. 14, 2014 (7 pages).

* cited by examiner

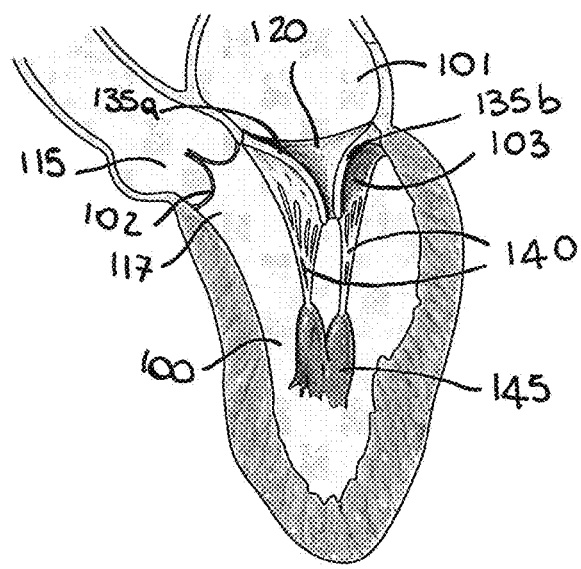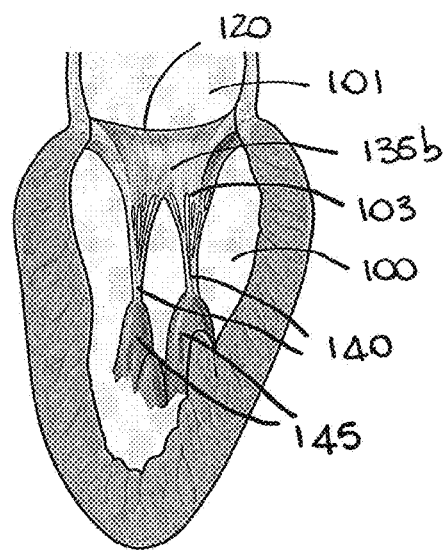
FIG. 9a    FIG. 9b
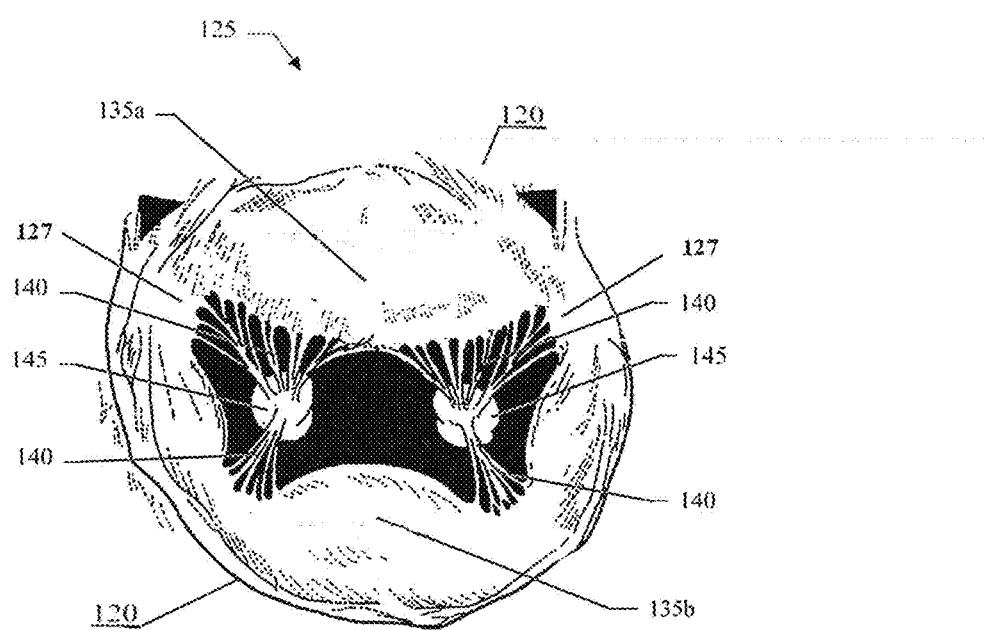
FIG. 9c

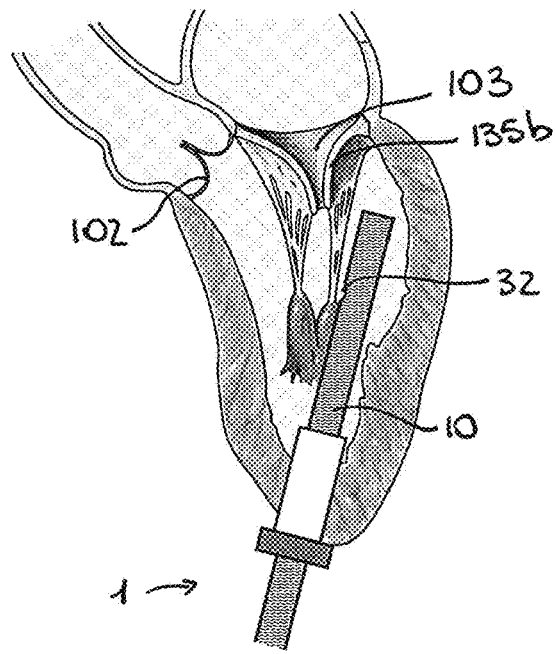
FIG. 10a1
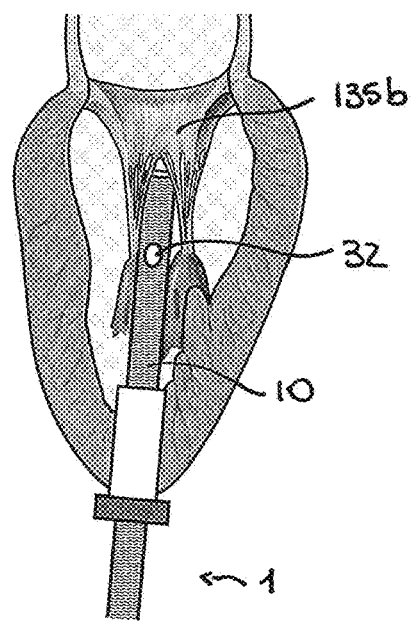
FIG. 10a2
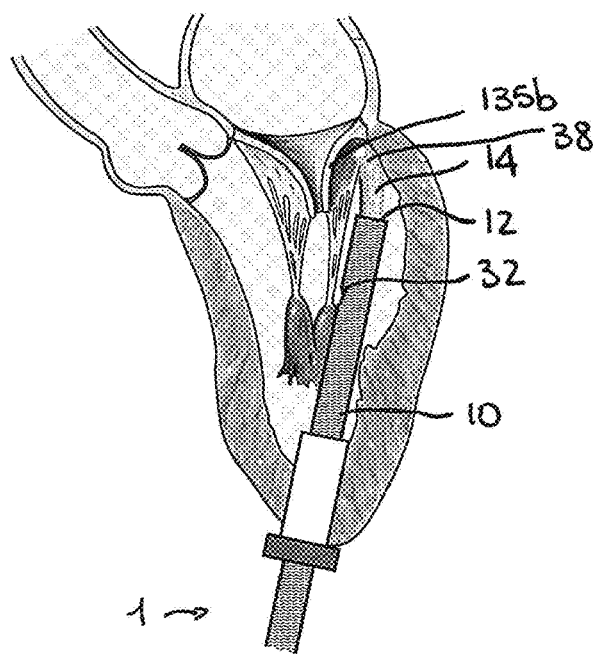
FIG. 10b1
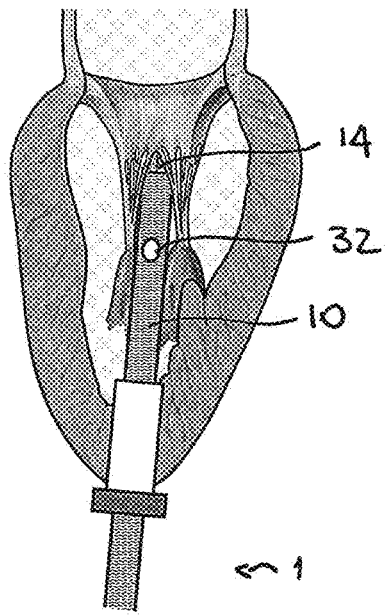
FIG. 10b2

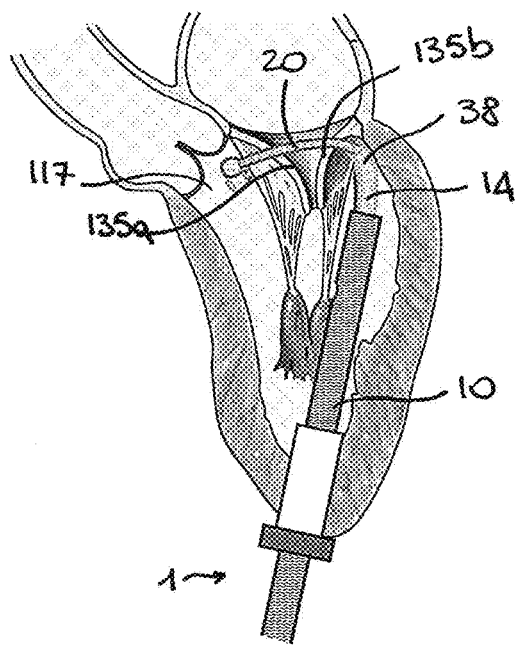
FIG. 10c1
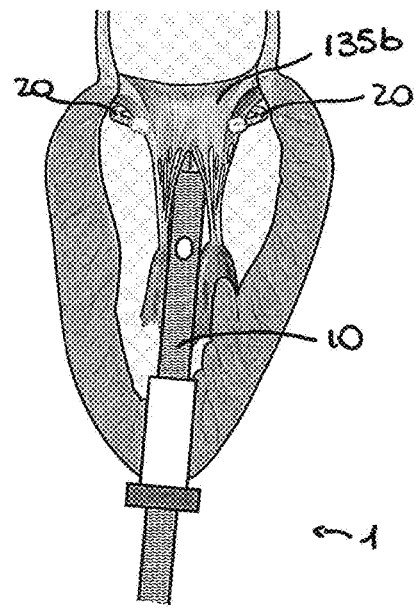
FIG. 10c2
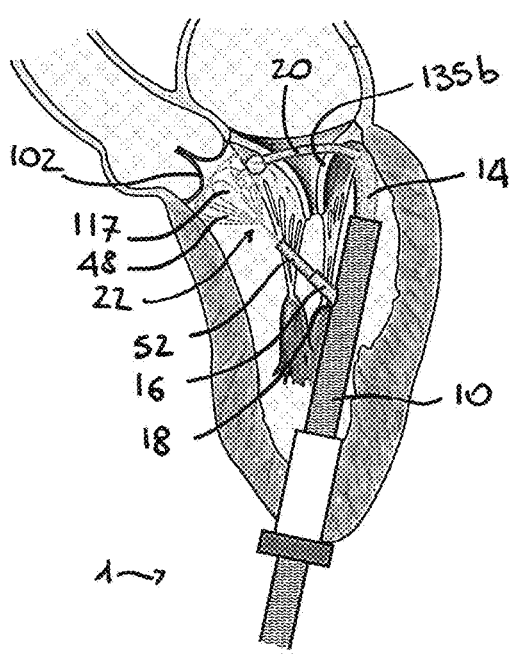
FIG. 10d1
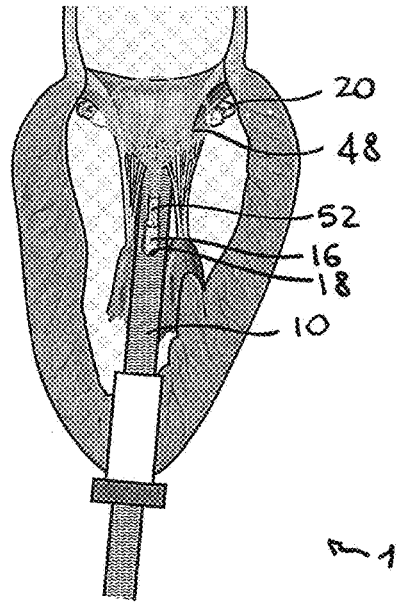
FIG. 10d2

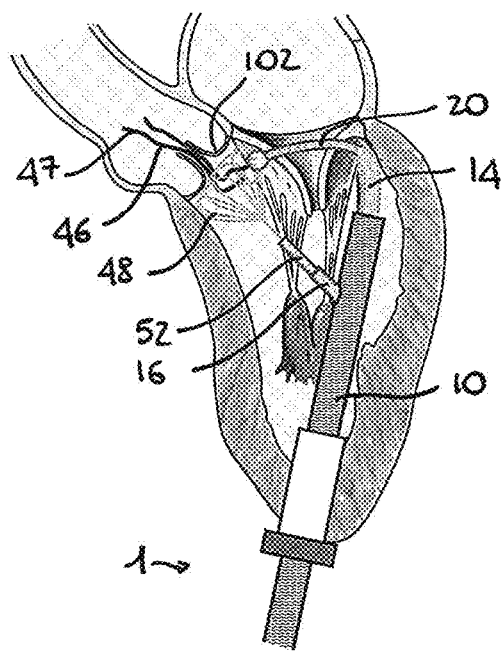
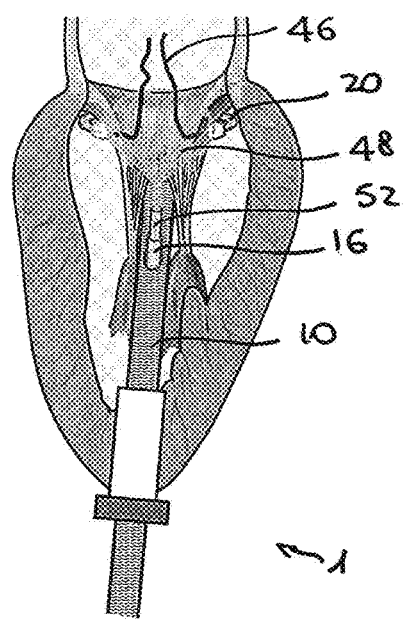
FIG. 10e1    FIG. 10e2
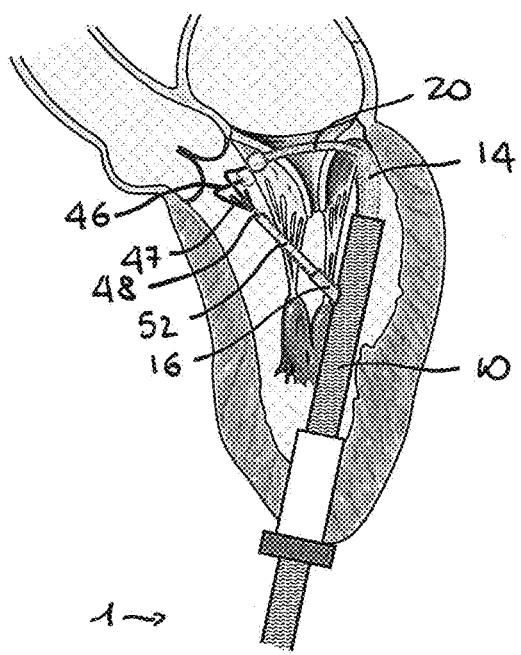
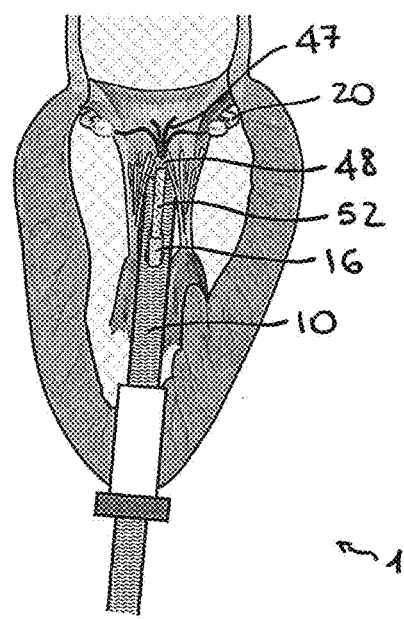
FIG. 10f1    FIG. 10f2

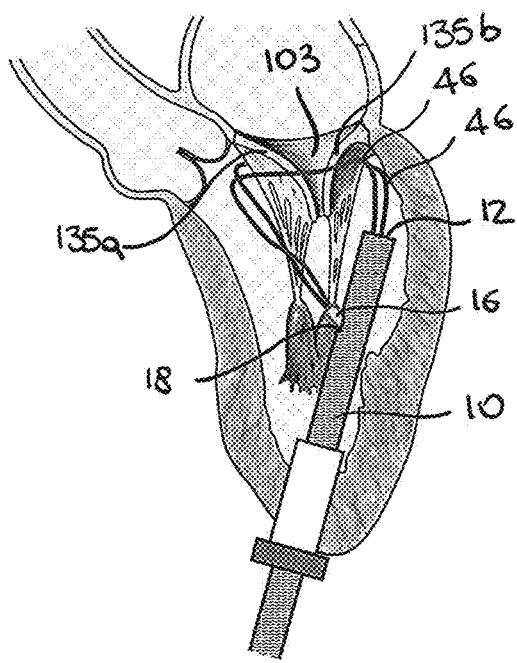
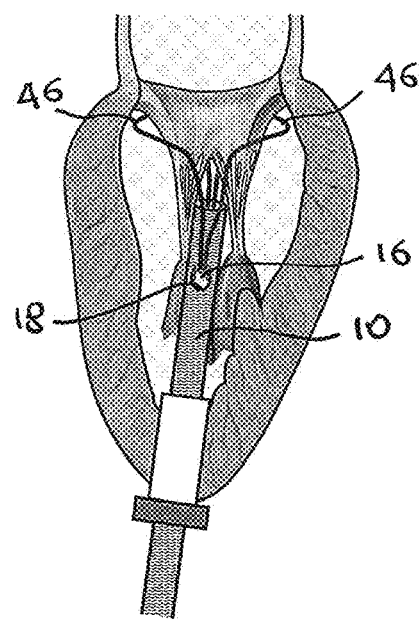
FIG. 10g1    FIG. 10g2
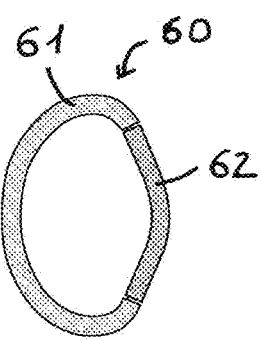
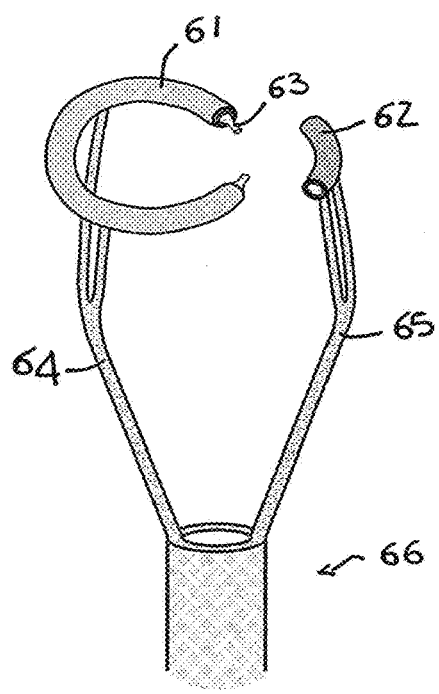
FIG. 11a
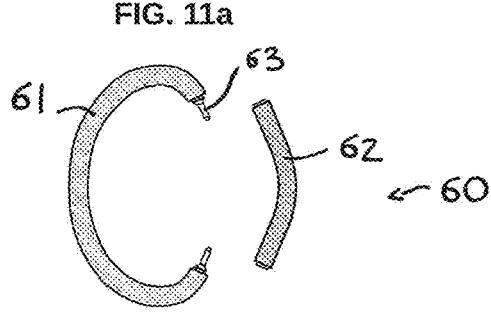
FIG. 11b    FIG. 12

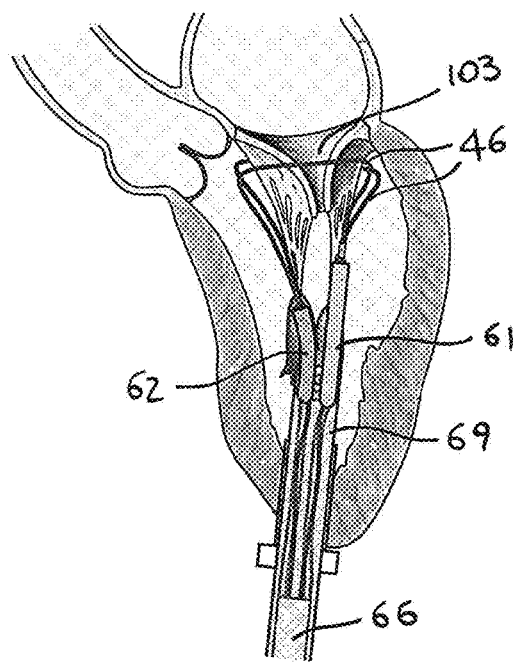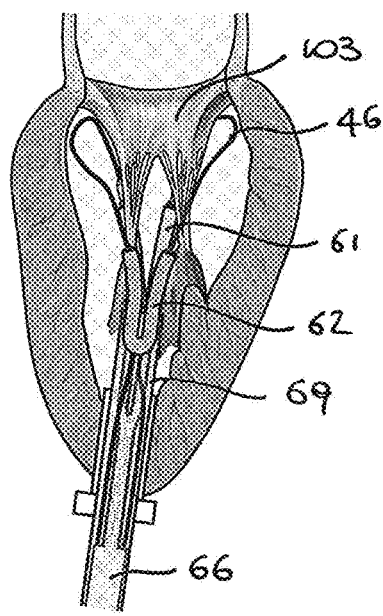
FIG. 14a1  FIG. 14a2
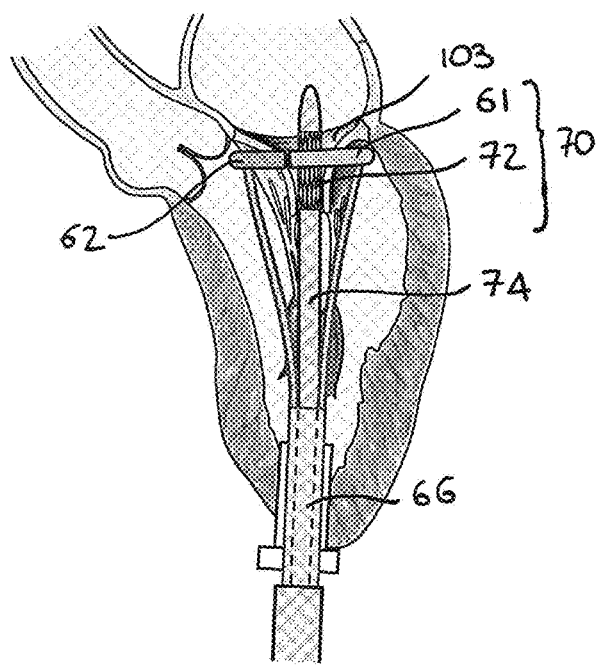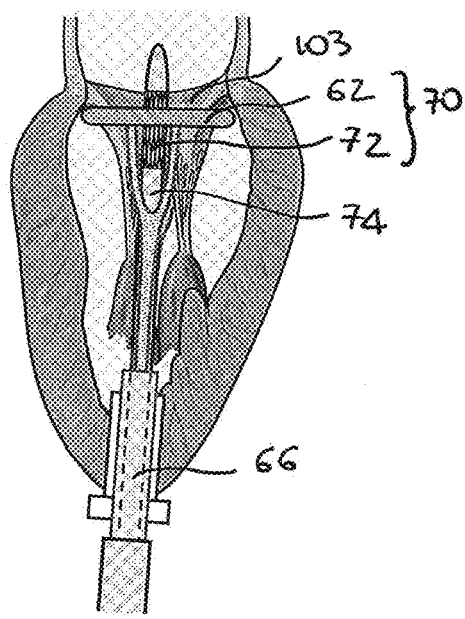
FIG. 14b1  FIG. 14b2

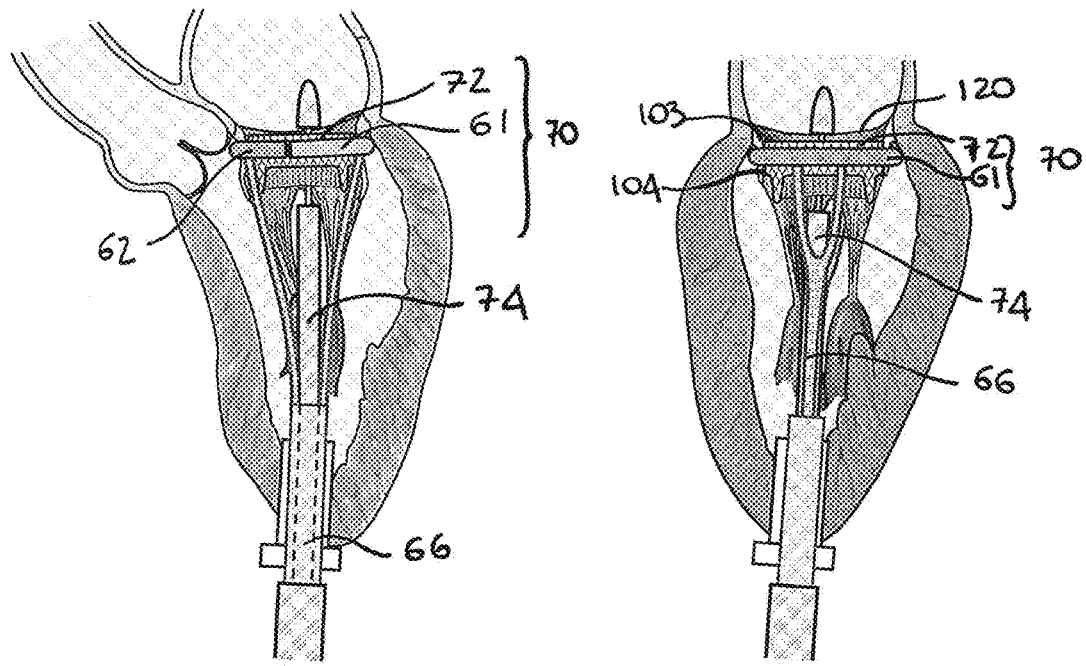
FIG. 14c1    FIG. 14c2
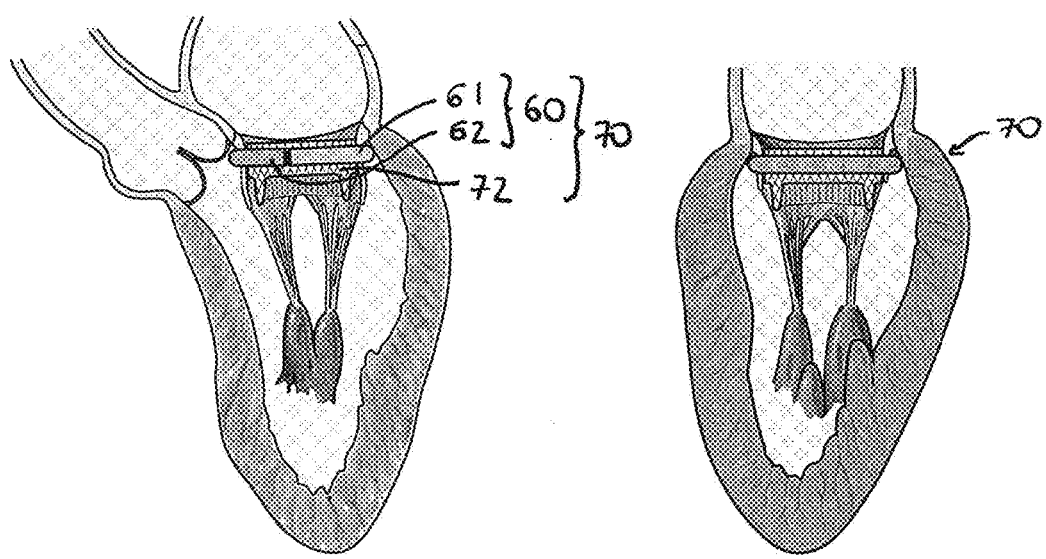
FIG. 14d1    FIG. 14d2

DEVICE FOR THE DEPLOYMENT OF A SYSTEM OF GUIDE WIRES WITHIN A CARDIAC CHAMBER FOR IMPLANTING A PROSTHETIC HEART VALVE

RELATED APPLICATION

This is a continuation of International Application PCT/IB2013/060249, with an International filing date of Nov. 19, 2013 (with a priority date of Nov. 20, 2012) and International Application PCT/IB2013/060250, with an International filing date of Nov. 19, 2013 (with a priority date of Nov. 20, 2012).

TECHNICAL FIELD

The application relates to systems, devices and methods for supporting transcatheter procedures for the therapeutic treatment of dysfunctions associated with cardiac pathologies.

BACKGROUND OF THE INVENTION

Historically, the corrective treatment of dysfunctions related to the main cardiac pathologies has been associated with surgical procedures which are highly invasive for the patient and are frequently accompanied by high intraoperative mortality. A typical example of these procedures is that of the replacement or repair of malfunctioning heart valves. In such a case, the surgical procedure generally includes the surgical opening of the chest, the emptying of the heart, requiring extracorporeal circulation in what are known as heart-lung machines, and the surgical opening of the heart itself to provide direct access to the malfunctioning heart valve. The treatment of the valve requires either its reconstruction by surgical methods, often with the support of prosthetic devices such as annuloplasty rings, or its complete removal and replacement with an artificial prosthesis. Clearly, this procedure, although necessary for survival, represents a serious trauma for the patient. In some cases, the patient's general condition, for example old age and the presence of concomitant pathologies, mean that the risks of mortality associated with these surgical procedures are so high as to be considered unacceptable. Consequently the patient must be denied to surgical treatment, and thus loses his access to a therapy which is essential to the improvement of his quality of life and any expectation of long-term survival. Recently, methods of treatment and correction of cardiac pathologies have been developed with the aim of providing the same efficacy as surgical treatment, but with a drastic reduction in the invasiveness of the procedure, thereby greatly decreasing the incidence of intra- and post-operative complications and almost completely eliminating discomfort for the patient. These methods are essentially based on the use of catheters, from which the general term "transcatheter methods" is derived, as well as endoscopic instruments and special prosthetic devices. These devices may be reduced in their overall dimensions during their introduction into the cardiac cavities via access ports with low invasiveness (for example, transfemoral, transvenous, transapical and other accesses), and then deployed in their operating configuration when the implantation site has been reached.

In this context, one of many possible examples is that of the implantation of valve prostheses by transcatheter methods in native aortic valves that have become stenotic, in other words malfunctioning, because of massive calcification of the leaflets.

These methods usually require a set of devices, ancillary to the procedure, which are intended to make the procedure safer, faster and more effective. Staying with the example of the transcatheter implantation of an aortic valve prosthesis, it is normal practice for the first step of the procedure to be that of crossing the malfunctioning valve with a guide wire, usually metallic, this guide wire being introduced through the access which is subsequently used for the implantation system, after which the catheter which carries the prosthesis itself to the implantation site is made to slide along the guide wire. This preliminary positioning of the guide wire makes the catheter navigation more reliable and effective, while reducing the duration and risk of the procedure.

In the same field of the treatment of malfunctioning heart valves by transcatheter methods, treatments for restoring valve function characterized by low invasiveness are under development also for the mitral valve. For example, a recent patent application, PCT WO2012063228, describes a prosthetic system capable of replacing the function of an atrio-ventricular heart valve, in other words a mitral or a tricuspid valve. In this system, a substantially annular structure is deployed around the native valve, surrounding the whole valvular and subvalvular apparatus. The correct operation of the prosthetic body which is subsequently released depends to a great extent on the correct positioning of the annular structure around the native valve. In fact, the annular structure must surround the whole native valve, while also being positioned immediately below the anatomical plane of the annulus, in contact with its ventricular side. In this case also, the preliminary positioning of guide wires is claimed to make the procedure safer, more effective and more reliable. Furthermore, the possibility of checking the correct positioning of the guide wires before the start of the deployment of the prosthetic component, and repositioning them if necessary, makes the procedure fully reversible.

The use of a guide wire for guiding a catheter along a given path into a cardiac cavity is also described, for example, in the patent application US2009234318. This specific invention relates to a method for repairing a mitral valve damaged by dilative pathology. In this case, the catheter surrounds only a portion of the mitral valve. By means of the catheter, anchoring members interconnected by a wire are implanted into the corresponding portion of the mitral annulus. The tensioning of the wire is claimed to have a restraining action on the mitral valve, thereby remodelling its shape and thus restoring its function, at least partially. In this case also, the first step in the procedure is that of deploying a guide wire around the posterior portion of the mitral valve. In this case also, the positioning of the guide wire along a path dictated by precise anatomical criteria ensures the correct outcome of the reconstruction procedure. However, this application does not describe any specific device, nor any particular procedure, for correctly positioning the guide wire according to the specific requirements of the therapeutic system.

The two applications described above are mentioned solely by way of example, and are not intended to limit the multiplicity of therapeutic treatments that could make use of a device capable of releasing a system of guide wires in an accurate and controllable way in the cardiac cavities.

WO2012/004679 discloses two different embodiments of a known device for inserting guide wires in a heart, both having an introducer catheter with a single lumen, in which enter one or two catheters.

WO2011/109813 describes a systems used to deliver a prosthetic heart valve to a deficient valve. An introducer catheter with a single lumen is used to introduce in the heart two angled catheters that can be maneuvered around the valve; a magnet at their end enables to stick them together forming a single hollow tube embracing the valve.

US2012/289945 discloses a retrieval device with releasably attached loops. The retrieval device may further comprise a delivery conduit configured to receive both a snare shaft and a guidewire in one or more lumens.

US2007/233239 describes an apparatus for modifying the annulus of a cardiac valve to reduce regurgitation of blood flow through the cardiac valve.

SUMMARY OF THE INVENTION

The present invention is intended to overcome the problems of the prior art and in particular to provide devices in support of transcatheter procedures for the therapeutic treatment of cardiac dysfunctions requiring navigation within the cardiac cavities along predetermined paths to meet specific requirements. More specifically, one object of the present invention is to enable one or more guide wires to be positioned precisely around an atrioventricular heart valve, for example the mitral valve. A further object is to provide for the creation of a system of guide wires which, by acting together in combination, surround the whole periphery of the atrioventricular valve, without penetrating, even partially, the bundles of chordae tendineae which form part of the subvalvular apparatus of the valve. Another aim is to provide for the creation of a guide wire path which is already directly positioned adjacent to the ventricular side of the native valve annulus; in other words, a guide wire path directly created in the immediate vicinity of the ventricular side of the insertion lines of the native leaflets in the valve annulus, along an anatomical groove lying immediately below the annulus. This is because the presence of chordae tendineae passing through the space at the rear of the native valve leaflets, called the second and third order chordae tendineae, makes it impossible in most cases to move guide wires, which are initially placed at a lower level in the ventricle, for example at the level of the free margin of the leaflets or at the level of the main chordae tendineae, to the position immediately below the annulus, in other words the position close to the insertion line of the leaflets. Briefly, the present invention is intended to simplify and accelerate the operation of placing guide wires along predetermined paths in the proximity of the annulus of a valve, especially of a mitral valve, while minimizing the risk of errors and the time required. A further object is to position the guide wires correctly so as to permit the correct deployment of the annular component of a prosthetic system for transcatheter replacement of the mitral valve described in the aforementioned patent application WO2012063228, as well as the correct deployment of a new and particularly effective prosthetic system which is described below.

The solution according to one or more embodiments of the invention, together with further characteristics and the advantages thereof, will be understood more fully by reference to the following detailed description, given purely for guidance and in a non-limiting way, to be read in conjunction with the attached drawings (in which, for the sake of simplicity, corresponding elements are indicated by identical or similar references and their explanation is not repeated). In this context, it is expressly intended that the drawings are not necessarily to scale (some details may be exaggerated and/or simplified) and that, unless specified otherwise, they are simply used to provide a conceptual illustration of the structures and procedures described. In particular:

BRIEF DESCRIPTION OF THE DRAWINGS

FIGS. 9a-9c show different sectional views of a human heart, with particular attention to the anatomy of the left ventricular chamber.

FIGS. 10a1-10g2 show details of an example of a procedure for positioning a system of guide wires around the native mitral valve, using the device of FIG. 1.

FIGS. 10a1-10a2 show the positioning of the introducer catheter in the left ventricular chamber.

FIGS. 10b1-10b2 show the positioning of a pair of guide catheters forming the first stage of the device.

FIGS. 10c1-10c2 show the positioning of a first and a second catheter forming the second stage of the device.

FIGS. 10d1-10d2 show the positioning of a capture system, with the capture device expanded immediately below the plane of the annulus of the aortic valve.

FIGS. 10e1-10e2 show the positioning around the mitral valve of a pair of guide wires introduced into the left ventricular chamber through the second stage and advanced into the subaortic space until their distal ends pass through the mesh of the capture device.

FIGS. 10f1-10f2 show the distal ends of the pair of guide wires captured by the capture device, the sheath of which has been advanced into the subaortic space.

FIGS. 10g1-10g2 show the system of guide catheters forming the first and second stages of the deployment device removed from the left ventricle, while the guide wires are kept in position around the mitral valve.

FIGS. 11a-11b show an example of an annular structure for anchoring transcatheter valve prostheses for atrioventricular valves, which can benefit significantly from the use of a system of guide wires positioned with the device of FIG. 1.

FIG. 12 shows the annular structure pre-mounted on an example of a positioning and support device.

FIGS. 14a1-14d2 show details of an example of a procedure for transcatheter implantation of a prosthetic system for mitral valve replacement, the system being formed by a collapsible valve prosthesis and the annular structure of FIG. 11a, using guide wires previously positioned by means of the device of FIG. 1 as a guide for the implantation.

FIGS. 14a1-14a2 show the step of introducing the annular structure into the left ventricle.

FIGS. 14b1-14b2 show the step of positioning a collapsible valve prosthesis after the assembly of the annular structure.

FIG. 14c1-14c2 show the step of releasing the collapsible valve prosthesis.

FIGS. 14d1-14d2 show the result of the procedure of implanting the prosthetic system on the mitral valve, after the removal of the devices that are ancillary to the implantation procedure.

DESCRIPTION OF THE PREFERRED EMBODIMENTS

Figure 1:
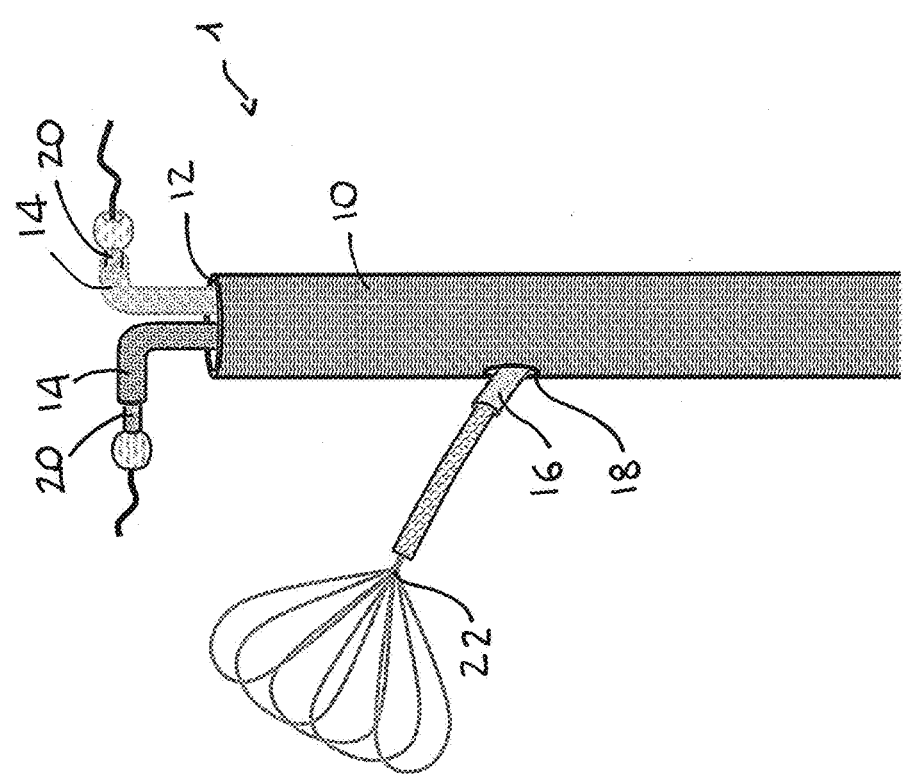
FIG. 1 shows an overall schematic representation of a device for deploying guide structures for operational procedures within the cardiac chambers (also referred to hereafter as a "device") according to one embodiment of the invention.

With reference to FIG. 1, this shows an overall schematic representation of a device 1 for deploying guide structures for operational procedures within cardiac chambers according to one embodiment of the invention. The device is composed of various components having the principal purpose of being introduced in a non-invasive manner into a cardiac chamber and of navigating therein along desired paths controlled by the operator. The device has been devised so as to be usable with a beating heart, and therefore without any need for extracorporeal blood circulation, without significantly interfering with the operation of the native heart valves, thus making the procedure entirely atraumatic and reversible. The procedure in progress can be interrupted at any time and the components of the device can be removed from the cardiac chamber without any effects on the function of the heart itself. Finally, the device is characterized by a small radial overall dimension and a smooth profile, free of discontinuities, making it particularly suitable for introduction into the cardiac cavities by transcatheter procedures.

The device 1 is essentially composed of a central body 10, called the introducer, formed by a multi-lumen guide, in other words one provided with various separate passages 12, 18 (also known as lumens) provided within it, and has the primary purpose of creating the access channels to the cardiac chambers for the individual instruments that are intended to operate within the heart. These instruments may be of various types, since they are intended for specific purposes. For example, they may be guide catheters with their terminal parts pre-shaped in a permanent and non-adjustable way. Guide catheters of this type may simply have their terminal parts bent at a predetermined angle, so as to deflect at this angle the devices that are advanced inside them. Alternatively, they may have their distal parts pre-formed in more complex curves or profiles which make them particularly suitable for specific anatomical situations. Other types of catheter that can be used in the device shown schematically in FIG. 1 may include catheters or guide catheters fitted with a deflection system which is adjustable during the procedure according to the operator's requirements. With this type of mechanism, known in the prior art as a steering mechanism, the catheter can be deflected and/or curved by an amount determined by the operator according to the requirements of the procedure. This degree of freedom makes the catheter better adapted and more controllable in its navigation within the anatomical structures whose configuration is difficult to predict.

Owing to the possibility of rotating the catheter in a direct and effective way (without effects of hysteresis or elastic effects), or the possibility of providing it with multiple deflection systems on different planes, the steerability of this type of catheter is almost total, enabling it to be navigated in a controlled way in three-dimensional spaces.

Since it generally has an inner lumen, any guide catheter can obviously be used for positioning a guide wire, or for positioning another catheter having an outside diameter compatible with the diameter of the lumen of the preceding stage.

Other instruments that can be used in the application of the device shown schematically in FIG. 1 also include, without limiting the general nature of the invention, endoluminal devices, known in the prior art as snaring devices. These devices, usually composed of collapsible looped structures made of metallic or polymeric materials, are particularly suitable for capturing the free ends of guide wires or catheters of small gauge. This is because they have structures that expand in space to generate a capture volume. The free ends of catheters or guide wires or similar devices passing through the capture volume are trapped by the structure when it is re-collapsed by a procedure which is usually the reverse of the expansion procedure. In this way, the distal end of a catheter or of a guide wire can be secured in a given position, or can be recovered to the outside of the cardiac chamber along the same path as that used for inserting the capture system. Endoluminal operating instruments of other types and with other functions can conveniently be used in the spirit of the invention described here, in order to deploy guide structures for operational procedures in the cardiac chambers.

FIG. 1 shows, in particular, a specific embodiment of the invention, particularly suitable for use in a ventricular chamber with access through the wall of the ventricle in the proximity of the apical region of the heart. As is shown more fully and in greater detail in the subsequent figures (FIG. 2 to FIG. 6), the whole device is composed of a double-lumen introducer member 10, a pair of guide catheters 14 preformed at their distal ends with a fixed curvature, having dimensions compatible with their advance within the main lumen 12 of the introducer, a guide catheter 16 which is substantially rectilinear but flexible, having dimensions compatible with its advance within the lateral lumen 18 of the introducer, a pair of catheters 20 which are substantially rectilinear but are fitted in their distal regions with an adjustable deflection mechanism and have overall radial dimensions compatible with their advance within the first set of guide catheters, and a capture device 22, having radial dimensions compatible with its advance within the lateral guide catheter.

The object of this device may be, for example, the positioning of guide wires, introduced and advanced in the ventricle through the second set of guide catheters, following paths determined by the operator and formed by the navigation of the second set of guide catheters in the cardiac chamber. The distal ends of these guide wires can then be captured by using the capture device, in order to hold them in a fixed position in the ventricular chamber or in order to draw them to the outside of the heart and make them accessible to the operator.

Figure 2:
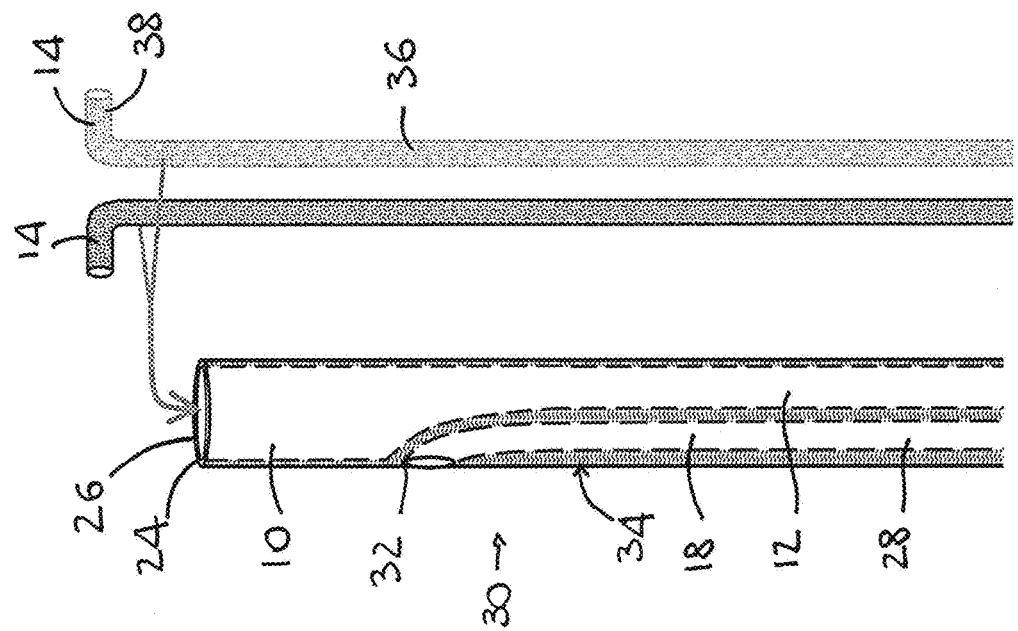
FIG. 2 shows an example of an introducer catheter with a double lumen, which is a component of the device of FIG. 1, and an example of a pair of guide catheters, to be positioned in the principal lumen of the introducer catheter, to form the first stage of the device of FIG. 1.

It should be noted that the use of metallic materials and/or radiopaque markers makes the components of the device visible to X-rays and the intracardiac procedures can therefore be guided by means of fluoroscopic visualization. In some cases, echocardiographic support may also be useful. With reference to the specific embodiment of the device depicted in FIG. 1, FIG. 2 shows a possible solution for the construction of the introducer catheter. The sectional view shows the double-lumen nature of this component in this specific embodiment of the invention. The first lumen 12, identified for the sake of simplicity as the main lumen, runs parallel to the main axis of the introducer catheter, the proximal orifice and the distal orifice 24 being positioned, respectively, at the proximal end and the distal end 26 of the catheter. The second lumen 18, identified for simplicity as the secondary lumen, is characterized by a rectilinear proximal portion 28, with the proximal orifice positioned at the proximal end of the introducer catheter. In the proximity of the intermediate region 30 of the catheter, however, the secondary lumen 18 is deflected towards the outside. The distal orifice 32 of the secondary lumen is therefore positioned on the lateral surface 34 of the introducer catheter. Thus the axis of advance of the main lumen is offset from that of the secondary lumen, at an angle determined by the curvature of the latter. An angle compatible with the intended use of this type of device may be within the range 15°-45°.

The constructional solution described above therefore creates an access route to two different areas of the cardiac chamber. The possible addition of further lumens, also characterized by an outward curvature at an intermediate level of the introducer catheter, would create access paths to different areas of the cardiac chamber. Still with reference to the specific embodiment depicted in FIG. 1, FIG. 2 also shows a set of guide catheters 14 that can be advanced in the main lumen 12 of the introducer catheter. In this specific embodiment of the invention, this first guide catheter stage is of the pre-formed type, with a substantially rectilinear proximal portion 36 and a distal end 38 pre-curved at about 90° with respect to the proximal portion 36. More generally, the object of this catheter stage is to deflect the axis of the devices that are advanced within it from a direction parallel to the axis of the introducer to a direction at an angle to the preceding one determined by the degree of curvature of the distal end of the guide catheter. Depending on the application, this angle may vary from 45° to 135° with respect to the axis of the proximal portion of the catheter, which is substantially parallel to the axis of the introducer. Thus the axis of advance of a device such as a catheter or a guide wire within the cardiac chamber is made to be independent of the axis required for its introduction into the heart. The guide catheters are free to rotate axially, and the distal curvature can therefore be orientated in different directions. In the specific embodiment shown in FIG. 2, for example, the distal ends 38 of the two guide catheters 14 of the first stage can be orientated along opposite directions. Consequently, the devices advanced in the lumen of the two guide catheters are deflected in the same plane perpendicular to the axis of the introducer catheter, but along paths extending in opposite directions. Clearly, it would also be possible to have a greater number of catheters forming the first stage, provided that this is compatible with the overall radial dimensions of the catheters.

The guide catheters 14 forming the first stage can be made from a polymeric or metallic material or from a combination of these. The material must be chosen so as to meet opposing requirements. This is because the terminal part 38 must be capable of being at least partially straightened when the guide catheter is made to advance within the main lumen 12 of the introducer, recovering its pre-formed configuration when it emerges into the cardiac chamber. On the other hand, the pre-formed part must be sufficiently rigid to deflect the device inserted into the lumen of the guide catheter. It is also preferable for the guide catheter forming the first stage to have characteristics of torsional rigidity, in other words to be capable of transmitting a torque from the proximal section to the distal section.

Figure 3:
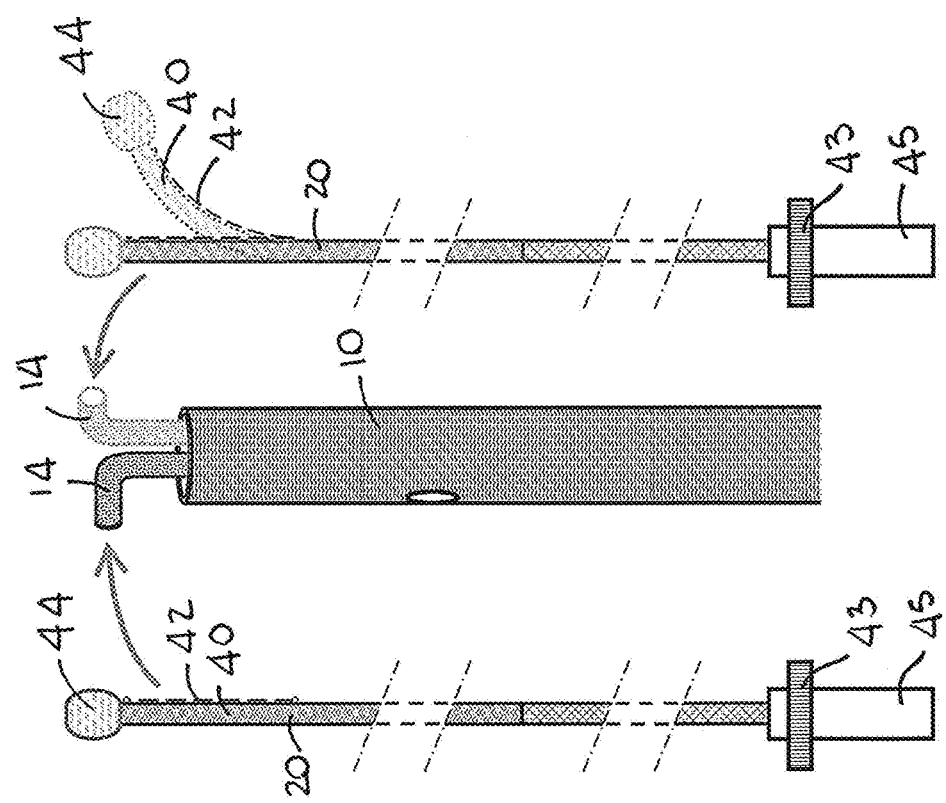
FIG. 3 shows an example of a pair of catheters, provided with controlled deflection mechanisms, forming the second stage of the device, to be coupled to the guide catheters of the first stage of FIG. 2.
Figure 6:
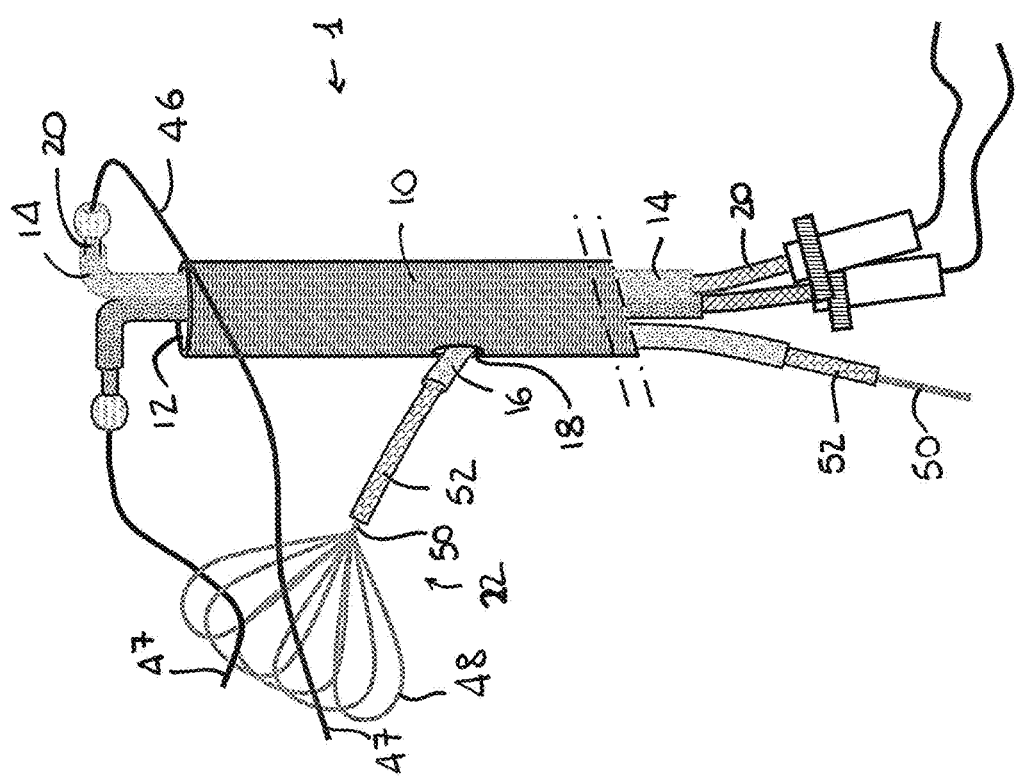
FIG. 6 shows an overall schematic representation of the device of FIG. 1, in the configuration in which the system of guide wires, positioned in the ventricular chamber through the first lumen of the introducer catheter, is captured by the capture system which is advanced through the second lumen of the introducer catheter.

Still with reference to the specific embodiment depicted in FIG. 1, FIG. 3 also shows a set of catheters 20, forming the second guide catheter stage, characterized by overall radial dimensions making them compatible with their advance within the lumens of the guide catheters 14 forming the first stage, as depicted in FIG. 2. In this specific embodiment of the invention, the catheter belonging to this second stage is substantially rectilinear and laterally flexible, so as to pass through the distal curvature of the guide catheter in which it is advanced, and is provided in its distal portion 40 with one or more deflection mechanisms 42, known as steering mechanisms, actuated by controls 43 positioned on the handle 45 at the proximal end of the catheter. By operating the control, a gradual and controlled deflection of the distal portion of the guide catheter can be achieved, so that the catheter becomes capable of navigation along paths determined by the operator, even in the most complex anatomical conditions. Preferably, the guide catheter is substantially rectilinear, with a substantially rigid proximal portion capable of transmitting a torque to the distal portion. The distal portion, extending at least halfway along the whole length of the catheter, is flexible enough to be deflected, while also being rigid with respect to torsion in a similar way to the proximal portion. Since the whole guide catheter can be rotated as a single unit simply by rotating the handle 45, without any significant elastic delay or hysteresis, even in the presence of the curvature created by the guide catheter 14 of the first stage, the navigation capacity of the second stage is considerably increased. In fact, each of the guide catheters 20 forming the second stage is free to slide and rotate within the guide catheters 14 forming the first stage of the system.

The optimal mechanical characteristics of the catheter, namely the high lateral flexibility combined with torsional rigidity, can be achieved by using correct constructional solutions for the catheter. For example, the use of an appropriate metallic reinforcement of wire mesh embedded in a polymer matrix to form the catheter wall is a constructional solution which provides high torsional rigidity, while preserving its bending deformability and avoiding any risk of collapse in bending (known as kinking). The distal end of the guide catheter forming the second stage, and that of the guide catheter forming the first stage, can be provided with an atraumatic tip 44 made in the shape of an olive or made of soft, deformable material adapted to prevent any possible damage to the walls of the cardiac chamber or of other anatomical structures present in the chamber, even in the case of accidental impact or friction of the catheter against them.

Figure 4:
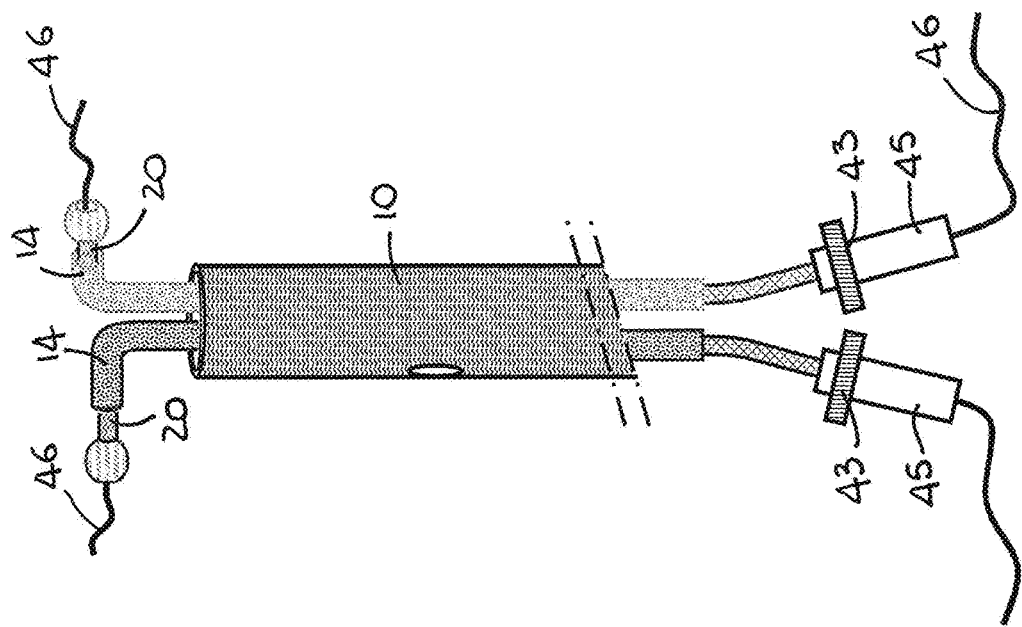
FIG. 4 shows the guide wires in the device.

FIG. 4 shows how the catheters 20 forming the second stage have inner lumens allowing the passage of devices for interventional procedures, such as smaller gauge catheters or guide wires 46 (as shown in the drawing) which can then be inserted into the proximal opening of the catheter and made to advance along its inner lumen until they reach the cardiac chamber by emerging from the distal end of the catheter 20. The guide wires 46 are inserted into the proximal orifice of the guide catheter and are made to advance therein until they emerge from the distal orifice, within the cardiac chamber, at the point and along the path made accessible by the system of guide catheters 14 and 20 of the first and second stages.

Figure 5:
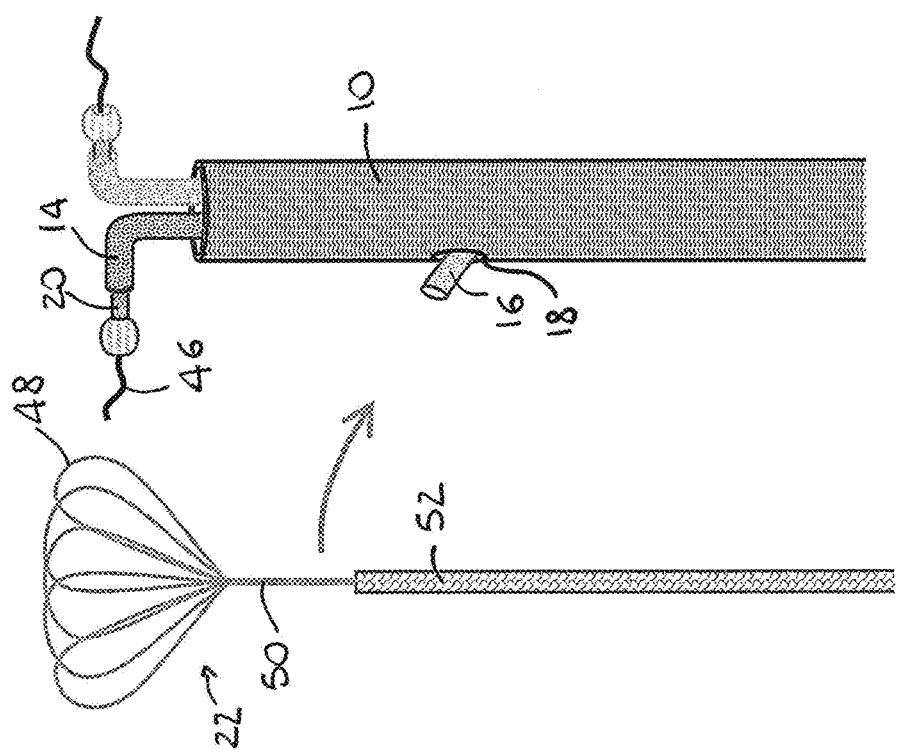
FIG. 5 shows an example of a guide catheter positioned in the second lumen of the introducer catheter to form the lateral stage of the device, and an example of the guide wire capture system to be inserted into the guide catheter forming the lateral stage of the device.

Still with reference to the specific embodiment of FIG. 1, FIG. 5 shows the possibility of using the secondary lumen 18 of the introducer catheter 10 to advance devices for interventional procedures, for example a further guide catheter 16 (also called a lateral stage) in a direction offset from the axis of the introducer, as shown in the drawing. Guide catheters of the type depicted in FIGS. 2 and 3 can also be used through the secondary lumen 18. This lateral guide catheter creates an additional access way to the cardiac chamber, in a different direction from that of the main system of guide catheters. FIG. 5 shows how, in a specific embodiment of the invention, an endoluminal capture device 22 (snaring device) can be introduced into the cardiac chamber through the guide catheter 16 inserted into the secondary lumen of the introducer catheter. In the specific embodiment of the invention shown in the drawing, the capture device 22 is represented as a set of loops 48 of metallic wire, with highly elastic properties, whose points of origin are joined together at the distal end of a stem 50 which is also metallic. The stem 50 is thin and flexible, and can adapt to the curvature of the path to be followed for its access to the ventricle. The proximal end of the stem is accessible to the operator, so that the positioning of the capture device can be controlled. The loop structure shown on the drawing is easily collapsible into a thin-walled, small gauge sheath 52 (also shown in FIG. 5), on removal of which the distal structure immediately returns to its expanded configuration. In other words, the positioning of the sheath relative to the capture device determines the configuration of the latter, which is collapsed if the sheath covers the device, or expanded if the sheath is retracted at the position of the stem.

Because of the multiplicity of loops 48 and their flower-like configuration, this device is capable of multidirectional capture, so that its orientation relative to the device to be captured becomes less critical. A wire only needs to pass in any direction through one of the loops of the expanded device in order to be captured when the device is collapsed again. Clearly, there is a wide variety of possible designs for the structure of the capture device, and these designs may also vary according to the particular function to be provided or any particular requirements to be met. Most of these designs are known in the prior art. By using materials with high mechanical performance, for example superelastic metal alloys such as Nitinol, for the capture device, and by using technopolymers such as polyamide or polyamide reinforced with a metallic mesh for the sheath, it is possible to limit the overall radial dimensions of the capture system (including the sheath and the capture device), making it compatible with endoluminal use; in particular, in the illustrated example, the diameter must be smaller than that of the lateral stage. More generally, the overall radial dimensions of systems currently in use for general endoluminal capture applications are within the range from 1 to 3 millimeters, although dimensions of less than one millimeter are also possible.

In the light of the specific solutions depicted in FIGS. 2 to 5, FIG. 6 shows an overall schematic representation of a device for deploying guide structures for interventional procedures within cardiac chambers according to one embodiment of the invention in its operating configuration. By using the main lumen 12 of the introducer catheter 10, positioned through the outer wall of the heart to provide an access port to the cardiac chamber, the operator can position the guide catheters 14 and 20 of the first and second stages according to his requirements, following the paths required by the application. In the case of the catheters 20 of the second stage, the various degrees of freedom available in the movement of the distal end of the catheter (axial advance, rotation about its own axis, adjustable deflection mechanism) are such that the desired paths can be followed and the final positions can be reached even in the presence of particularly unfavourable anatomies. The operator can introduce a capture system 22 into the cardiac chamber through the guide catheter 16 positioned in the secondary lumen 18 of the introducer catheter 10, determining the end position of the system by means of the control stem 50 and modifying its configuration (expanded or collapsed) by acting on the corresponding containing sheath 52. Because of the specific geometry of the secondary lumen 18, the axis of the capture device 22 is offset with respect to the catheters of the main lumen 12, making its action simpler and more effective. This is because the operator can advance guide wires 46 within the lumens of the catheters forming the second stage until they emerge into the cardiac chamber so that their distal ends 47 can be gripped by the capture device 22. The capture device can be used, for example, to stabilize the distal ends of the guide wires, in support of subsequent intracardiac operations.

Figure 8:
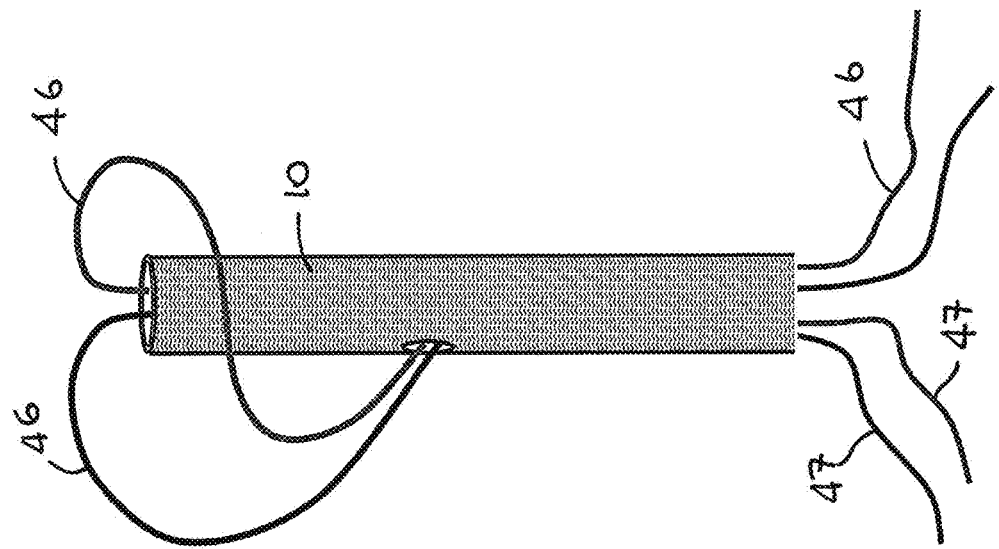
FIGS. 7 and 8 show an overall schematic representation of the device of FIG. 1, in the configuration in which the distal ends of the guide wires are recovered to the outside the cardiac chamber by the capture system.
Figure 7:
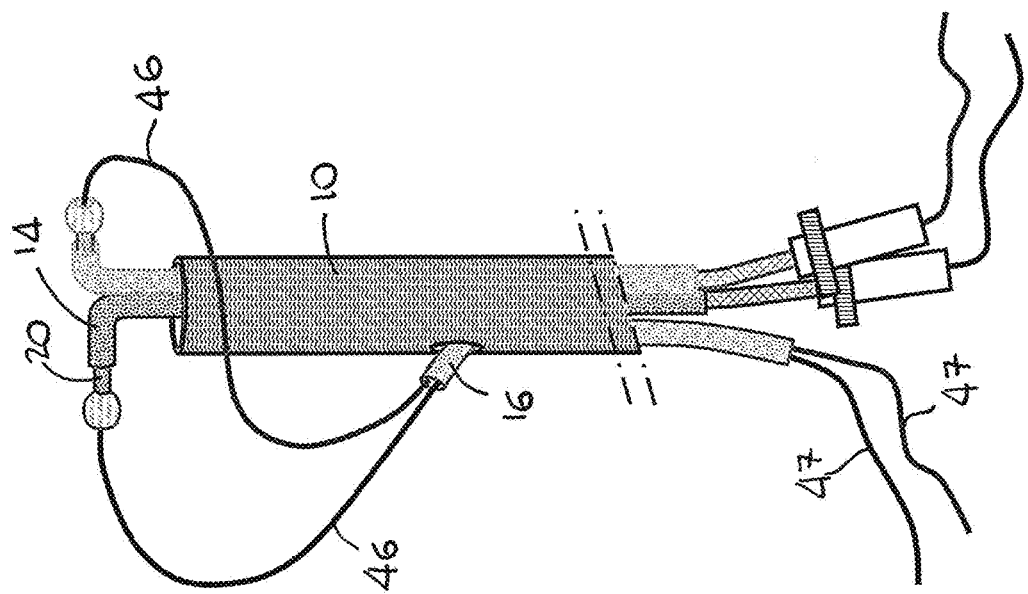

FIGS. 7 and 8 show a use of the capture device which differs from that described above. In this example, the capture device 22 is used to recover the distal ends of the guide wires to a proximal position. This makes it possible to position one or more guide wires within a cardiac cavity along a path determined by the operator, who has access, at the end of the procedure, to both ends of the guide wire or wires used for the purposes of this procedure.

In a first step, the operator advances and positions the system of guide catheters 14, 20 by following the desired path (over all or part of its length). The guide wire 46 (or guide wires) is then introduced into the cardiac cavity through the inner lumen of the second stage guide catheter 20, causing it to emerge from the distal orifice of this catheter. The guide wire is advanced sufficiently within the cardiac cavity to allow it to be captured by the capture device 22. By removing the capture system from the cardiac cavity, the operator also recovers the distal end 47 of the guide wire (or guide wires). Thus one or more guide wires 46 can be positioned within the cardiac cavity along paths specified by the operator. At the end of the procedure, the operator has simultaneous access to the proximal ends and the distal ends 47 of the guide wires positioned in the cardiac chamber. FIG. 7 depicts the configuration of the device after the distal ends 47 of the guide wires 46 have been captured and the capture system 22 has been drawn out: the guide wires enter the cardiac cavity through the system of catheters 14, 20 inserted into the main lumen 12 of the introducer 10 and exit through the guide catheter 16 inserted into the secondary lumen 18. Finally, FIG. 8 shows the removal of the whole system of guide catheters, leaving in situ only the guide wires 46 which can thus be used as guide structures for subsequent interventional procedures.

To provide a detailed illustration of an exemplary application relating to the left ventricle of the device 1 for the deployment of guide structures for interventional procedures within cardiac chambers as depicted in FIG. 1, the diagrams of anatomical sections through a heart shown in FIGS. 9a to 9c will be used. In particular, FIGS. 9a and 9b show two views along the longitudinal axis of the left side of the heart, in other words views of sections which substantially cut the heart along the longitudinal axes of the two chambers of the left side, from the apex (in other words the lower point of the heart) to its top. These sections therefore show both the left ventricle 100 (the lower chamber, including the apex) and the left atrium 101 (the upper chamber). FIG. 9a shows the view obtained by taking a section through the left side of the heart along a plane identified by the nominal axis of the left ventricle and the axis of the aortic valve 102. In this case, the section plane cuts the mitral valve 103 along its anteroposterior axis, following the mid-line of the posterior leaflet and of the anterior leaflet, as well as taking a section through the aortic valve. This section therefore enables the aortic root 115 to be visualized with the aortic valve apparatus 102 and the aortic subvalvular chamber 117, usually referred to as the LVOT (left ventricle outflow tract). Both leaflets of the mitral valve, namely the anterior leaflet 135a and the posterior leaflet 135b, are also visible in section. The mitral valve separates the left atrium 101 from the left ventricle 100. The mitral annulus 120, the bundles of the chordae tendineae 140 and the papillary muscle 145 are other clearly identifiable anatomical structures. A single group of papillary muscles (and the corresponding chordae tendineae) is visible in this view. In the case of FIG. 9b, the view of the left side of the heart is shown as it appears if the section plane is rotated about the axis of the ventricle until it is aligned with the commissure-commissure axis of the mitral valve. This view shows only the posterior leaflet 135b of the mitral valve, with the corresponding portion of the annulus 120 and the corresponding subvalvular apparatus formed by the chordae tendineae 140 and papillary muscles 145. This section shows both papillary muscles (in section). Finally, FIG. 9c shows a plan view of the mitral valve from a supravalvular viewpoint, as it appears if the left atrium is uncovered. The anterior mitral leaflet 135a and the posterior leaflet 135b are visible. Both leaflets are surrounded and connected to the muscular structure of the left ventricle by the mitral annulus 120. The transition regions between the two valve leaflets along the annulus are the commissural regions 127. This view clearly shows the two main orthogonal axes of orientation of the mitral valve, namely an axis of symmetry in the anteroposterior direction, passing through both leaflets along the mid-line, and an axis orthogonal to the preceding one, aligned along the commissure-comissure direction. Finally, the bundles of the chordae tendineae 140 which secure the free margins of the valve leaflets to the papillary muscles 145 are visible through the orifice of the mitral valve.

FIGS. 10a1 to 10g2 show details of a possible procedure followed for the deployment of a system of guide wires to surround the native mitral valve 103, by inserting the system into the left ventricle through a transapical access, using the device 1 for deploying guide structures for interventional procedures within the cardiac chambers as depicted in FIG. 1 as a specific embodiment of the invention.

FIGS. 10a1 and 10a2 depict the initial step of the procedure in the two different sections through the left side of the heart. The same presentation mode is used in the subsequent drawings depicting this procedure. The drawings show the positioning of the distal end of the introducer catheter 10 adjacent to the ventricular wall, through a transapical access, at the rear of the posterior leaflet 135b of the mitral valve 103, on the mid-line of the latter. In this position, the introducer catheter 10 creates a direct access to the native annulus of the mitral valve, on its ventricular side. The introducer 10 must be orientated angularly on its axis in such a way that the distal orifice of the secondary lumen 32 is directed towards the aortic valve 102, in the direction along which the capture system is to be advanced. FIGS. 10b1 and 10b2 show, again in the two different views of the left-hand side of the heart, the positioning of the guide catheters 14 forming the first stage. These are advanced along the main lumen 12 of the introducer 10 until they are close to the plane of the mitral annulus, on the ventricular side. They are then orientated axially so that their curved distal ends 38 are both orientated tangentially to the mid-line of the mitral annulus, but in opposite directions. This orientation enables the catheters of the subsequent stage to be guided in a direction parallel to the mitral annulus. Because of the presence of radiopaque markers on the distal edge of this catheter, and on other components of the system, the orientation of the system can be visualized more immediately by means of X-ray based imaging systems (such as fluoroscopic systems).

FIGS. 10c1 and 10c2 show the positioning of the catheters 20 forming the second stage of the device, each of which surrounds one half of the mitral valve. The introducer 10 and the catheters 14 forming the first stage of the device are positioned on the back of the posterior leaflet 135b of the mitral valve, while the distal ends of the catheters 20 forming the second stage of the device face the back of the anterior leaflet 135a. The drawings show that the presence of a controlled deflection mechanism at the distal end of the catheters 20, as well as its capacity to be rotated axially, improves the control of the navigation of the distal end of the catheter. In specific regions of the mitral valve anatomy, for example the commissural regions, this is essential for the correct positioning of the catheter.

Both of the distal ends of the catheters forming the second stage of the device therefore face each other in the space below the aortic valve (called the LVOT) 117, immediately behind the anterior leaflet of the mitral valve.

FIGS. 10d1 and 10d2 show the positioning of the guide catheter 16 which forms the lateral stage of the device within the secondary lumen 18 of the introducer catheter 10, creating a further access route to the space below the aortic valve (LVOT) 117, in a direction which is offset from the nominal axis of the ventricle and from the plane of the mitral annulus (that is to say, the plane on which the catheters 20, forming the second stage of the device 1, lie), but which substantially coincides with the axis of the aortic valve. The capture system 22 in its low-profile configuration, with the capture device 48 completely collapsed inside the sheath 52, is introduced into the LVOT 117 through the lateral guide catheter 16. As shown in the drawings, the capture device 48 is subsequently released from the sheath 52 and expanded immediately below the aortic valve 102. The shape and position of the capture device 22 are such that it creates a kind of net entirely covering the portion of the left ventricle that opens into the aortic valve, in other words the LVOT 117, while not interfering with either the blood flow or the movement of the aortic valve leaflets. The design and the elastic characteristics of the capture device 22 are such that no interference is permitted either with the aortic valve 102, which would entail a risk of trauma to the native leaflets or to the annulus, or with the electrical conduction system (the atrioventricular node and the bundle of His) located on the septal side of the LVOT, which would entail risks of blockage of the left branch.

The distal ends of the catheters 20 forming the second stage of the device substantially face the capture device 22, on the ventricular side of the device.

FIGS. 10*e*1 and 10*e*2 show a pair of guide wires 46 advanced into the LVOT 117 from the two distal orifices of the catheters 20 of the second stage. The position of the catheters 20, together with the dragging action of the systolic blood flow, which is ejected from the left ventricle through the aortic valve, cause the guide wires to be pushed through the loops of the capture device 22, so that they are positioned across the aortic valve 102 up to rise through the aortic root and the ascending aorta. The use of the controlled deflection mechanism located at the distal end of the catheters 20 can also contribute to the guiding of the guide wires 46 through the capture device 22. It should be borne in mind that all the components described here (for example the guide wires and the capture device) are intrinsically radiopaque, or are made radiopaque by means of suitable markers (at the distal ends of the second stage catheters, for example).

FIGS. 10*f*1 and 10*f*2 show how the reclosing of the collapsible device 48 inside its containing sheath 52 causes the capture of the distal ends 47 of the pair of guide wires 46, which remain trapped in the loops of metallic wire of the capture device.

FIGS. 10*g*1 and 10*g*2 show the recovery to a proximal position of the sheath 52 and of the collapsible device 48 through the secondary (lateral) lumen 18 of the introducer catheter 10, and the recovery of the two pairs of guide catheters 14 and 20 forming the first and second stage, through the main lumen 12 of the introducer catheter.

Thus the distal ends 47 of the pair of guide wires 46 are also recovered to the outside of the left ventricle, leaving the guide wires 46 deployed around the mitral valve 103 with their proximal ends positioned inside the main lumen of the introducer catheter 10 and their distal ends positioned inside the secondary lumen of this introducer 10. The operator is thus provided with a system of guide wires which passes into and out of the left ventricle, after wrapping around the mitral valve 103, through the same apical port, but inside two different lumens 12, 18.

The introducer catheter 10 can then be removed, leaving in situ only the pair of guide wires 46 wrapped around the mitral valve. Both ends of each guide wire are recovered to the outside of the heart through the apical port. A system of guide wires has thus been fully deployed within a cardiac chamber along paths determined by the operator.

The principle described with reference to FIGS. 10*a*1 to 10*g*2 for a pair of guide wires can be extended to a greater number of guide wires, by means of an obvious modification of the deployment system depicted in FIG. 1, in which multiple access ways for guide wires are created through the main lumen of the introducer catheter. It will also be evident to anyone skilled in the art that the configuration shown in FIGS. 10*g*1 and 10*g*2, where a pair of guide wires surrounds the mitral valve 103, can easily be changed into a configuration with a single guide wire wrapped around the whole mitral valve. In fact, it is simply necessary to join the two corresponding ends of the two guide wires 46 and to recover one guide wire completely by recovering the other. In the configuration shown in FIGS. 10*g*1 and 10*g*2, the joining of the distal ends produces a guide wire which is entirely wrapped around the mitral valve, the loop being completed on the reverse of the posterior leaflet 135*b*. Conversely, if the proximal ends are joined, this produces the symmetrical configuration, in which the loop around the mitral valve 103 created by the guide wire which remains in situ is completed on the reverse of the anterior leaflet 135*a*.

In an example of application, not in any way intended to limit the general nature of the applications and operating procedures which can benefit from this device or have an extension of uses as a result of it, the use of the device for the deployment of the guide wires within the cardiac chamber in association with a transcatheter system for the replacement of an atrioventricular valve is described below with reference to FIGS. 11*a* to 14*d*2. The prosthetic system is made up of two components, namely a prosthetic valved body, to be expanded inside the native valve, and a substantially annular support structure, positioned so as to surround the outside of the native valve, and serving to create an anchorage and a sealing to backflow by entrapping between the two components the native leaflets at the level of the annulus.

The positioning of the annular structure is essential for the correct operation of the whole prosthetic system. To ensure the reliable anchorage of the prosthesis and reduce the risk of paraprosthetic fluid leakage, the positioning of the annular support structure must essentially meet two requirements, namely that the annular structure must be wrapped around the whole of the native valve, without passing through its orifice or the subvalvular apparatus, and that it must be positioned in contact with the annulus. A system of guide wires deployed immediately below the annulus of the native valve and capable of being wrapped around the whole of the valve therefore provides an effective guide for the positioning of the annular component. Furthermore, advantageous versions of the design of the annular support structure can be developed, because of the possibility of having a separate pair of guide wires accessible at both ends.

By way of example, without any intention to limit the general nature of the application, FIGS. 11*a*-11*b* show an annular support structure 60 made of two separate and independent components 61, 62, with a connection system 63 which enables permanent and durable structural continuity to be restored during the procedure of positioning and release at the implant site (FIG. 11*b*).

Each component 61, 62 of the annular structure can be anchored to the distal end of a separate support arm 64 and 65, forming part of the same positioning and support device 66 (FIG. 12). Alternatively, each component can be conveyed to the inside of the ventricular chamber by means of its own support and positioning device.

Figure 13B:
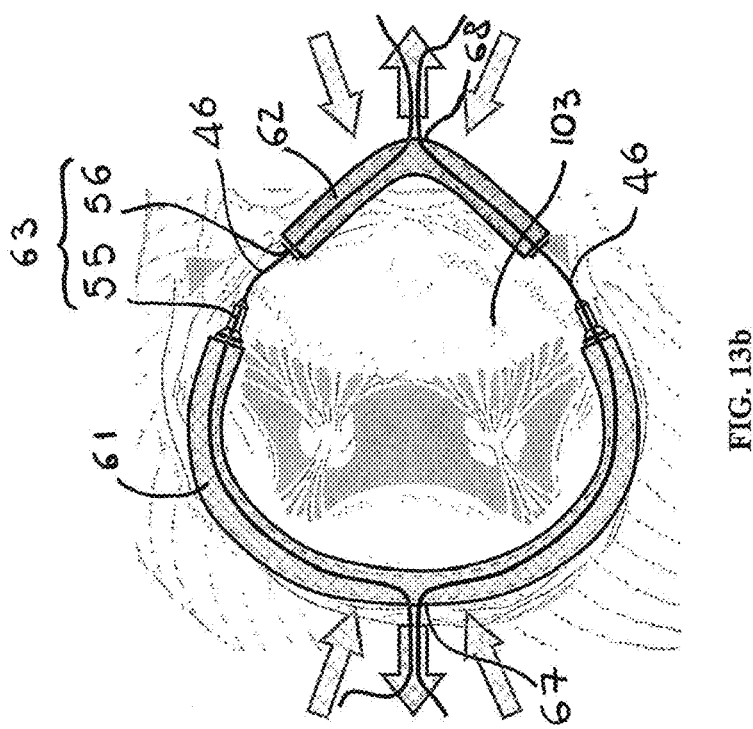
FIGS. 13a-13b show an example of the use of a pair of guide wires, previously positioned using a device according to FIG. 1, to guide the introduction and positioning of the annular structure of FIG. 11a. The components of the annular structure and the support structure are shown initially in the collapsed configuration and then in the released configuration.
Figure 13A:
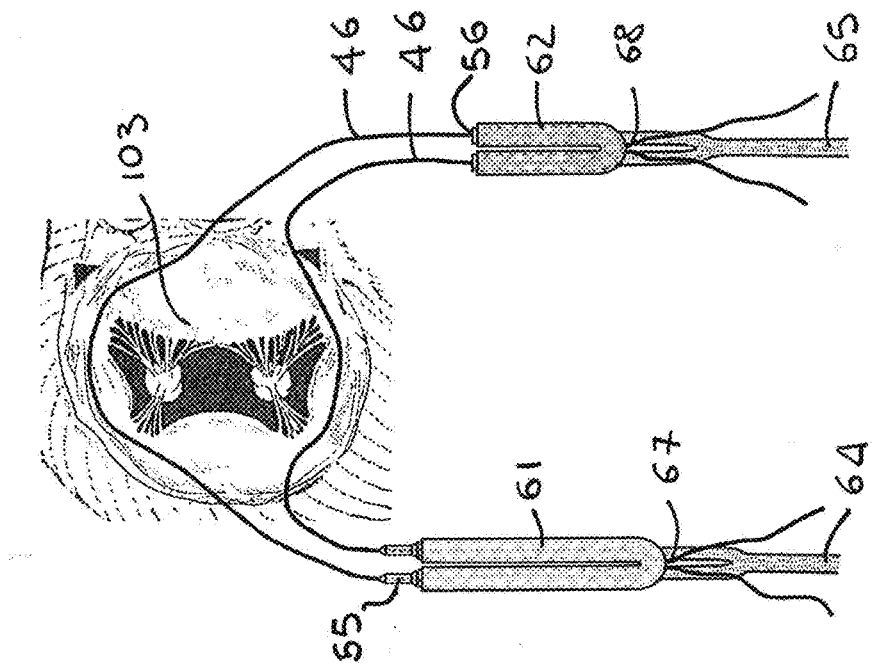

As shown in FIGS. 13*a* and 13*b*, the components 61 and 62 of the annular structure and the arms 64 and 65 of the positioning and support device 66 can all be deformed to provide a smaller overall radial dimension of the whole system, compatible with its introduction into the ventricular chamber through an apical access port. According to the present state of knowledge in the field of transcatheter heart valve treatment technology, the maximum diameter of the profile of the devices compatible with a transapical procedure is about 10 mm.

The drawing shows that the pair of guide wires 46, previously positioned around the mitral valve by the device 1 for deploying guide structures for interventional procedures as proposed by the present invention, can be used to guide the components 61 and 62 of the annular structure 60 inside the ventricular chamber. In fact, each component of the annular structure is made with a hollow ("over the wire") geometry, allowing the passage of a guide wire 46 and providing an aperture 67 and 68, located about halfway along the length of the component, for the exit of the wire. Each end of each guide wire 46 is then made to advance within one half of one of the components 61 and 62. The free end of the guide wire is inserted into the orifice at the free end of the component, and is made to emerge through the intermediate aperture 67 and 68. The sequence followed for the positioning of the guide wires 46 must be such that the corresponding halves of the two components 61 and 62 slide along the same guide wire, coming from the opposite ends (FIG. 13a). The two components 61 and 62 of the annular structure, when thus coupled to the guide wires 46, are then introduced by the two opposite ends of the system of guide wires and are advanced over the wire into the ventricular chamber until they surround the native mitral valve 103 in the correct manner, exactly at the subannular level where the guide wires 46 were positioned previously. The guide wires are then also essential for the alignment of the free ends of the components 61 and 62 of the annular structure in order to promote their reconnection (FIG. 13b). Finally, by suitably tensioning the guide wires 46, it is also achieved the effect of applying a closing action to the locking mechanism 63 between the two components 61 and 62 of the annular structure, tending to reduce the peripheral extension of the structure.

The locking mechanism 63 comprises pins 55 adapted to engage in suitable holes 56, and in particular it is composed of a pair of pins 55 and corresponding holes 56. Each end of one of the two components 61 is provided with a pin 55, while each end of the other component 62 is provided with a hole 56. The two components can be connected by inserting each pin into the corresponding hole.

FIGS. 14a1 to 14d2 provide a summary illustration of a possible procedure for implanting a prosthetic system for replacement of the mitral valve by a transcatheter technique and transapical route. The following description omits the preparatory procedure in which the two guide wires are positioned so as to surround the mitral valve, since already described above.

FIGS. 14a1 and 14a2 show, from two different views, the introduction and deployment (previously shown in FIGS. 13a and 13b) in the left ventricle of the two components 61 and 62 of the annular structure in their collapsed configuration, mounted on the positioning and support device 66. The whole system can be initially collapsed into a sheath 69 which can be used as an introducer. When its distal edge has arrived in the proximity of the mitral valve 103, the introducer is fixed, and, by means of the positioning and support device 66, the components 61 and 62 of the annular structure are deployed in the ventricle, while still being guided by the guide wires 46.

When the components 61 and 62 of the annular structure have been correctly positioned and interconnected with the aid of the guide wires, the central valved body 72 of the prosthetic system 70 is introduced, this body also being collapsed and mounted on a positioning and release device 74 which is fully integrated with the similar device 66 used for the annular structure (FIGS. 14b1 and 14b2).

The drawings show, without any intention to limit the general nature of the invention, a device 74 which slides coaxially with the support device 66 of the annular structure. The coaxial solution has the significant advantage of providing a practically perfect alignment with the orifice of the mitral valve. This significantly simplifies the design of the positioning and release device 74 for the central valved body 72.

The central valved body 72 is positioned across the mitral valve 103, in the final position before release. The main advantage of the complete mutual integration of the two devices 74 and 66 for positioning and releasing the components 61, 62 and 72 of the prosthetic system 70 is that the components can be positioned with respect to each other with great accuracy, without any particular requirements for skill on the part of the operator. Indeed, it is simply enough to provide a reference mark, of a mechanical, optical or other type, allowing to uniquely identify the configuration in which the components of the prosthetic system 60 and 72 are perfectly aligned for release and mutually positioned for optimal coupling with each other. In the example shown in the drawings, the structure of the device itself ensures the coaxial placing of the two components of the prosthesis. A simple mechanical stop, which arrests the axial sliding of the two parts of the release device of the prosthetic system at a precise position, also ensures optimal positioning immediately before the final release.

FIGS. 14c1 and 14c2 show the release of the central valved body 72 within the mitral valve 103 by the positioning and release device 74, which is integrated with the positioning and support device 66 of the annular structure 60. The central body expands, and thus, since the central valved body 72 is released within the mitral valve 103 and the annular structure 60 is positioned outside the mitral valve, in an immediately subannular position, the leaflets 104 of the native mitral valve 103 are entrapped between the two components. The leaflets, creating a continuity with the annulus 120 of the valve along the whole periphery of the prosthesis 70, provide an anchorage for the prosthesis 70 and a sealing to the backflow.

Finally, FIGS. 14d1 and 14d2 show the valve prosthesis 70 implanted after the removal of the release and support device through the apical port of the left ventricle. The advantages of the embodiment described above include not only the provision of a system of guide wires which ensures the correct positioning of the components 61 and 62 so that they wrap around the whole of the native valve at a subannular level, but also those deriving from the possibility of inserting the two components 61 and 62 of the annular structure 60 separately and on opposite sides; thus the introduction of the components 61 and 62 into the ventricular cavity is made simpler and safer, being the components shorter than those of an annular structure made in one piece. However, the primary advantage is that the annular structure can be held in position during the implantation procedure by means of the supports 64 and 65 distributed along the whole periphery of the component. These supports can be the same as those used for the introduction of the components into the ventricular chamber, and can be physically integrated with the positioning and release system 74 of the central valved body 72. In other words, when the system 66 for conveying, positioning and releasing the annular structure 60 is integrated with the corresponding system 74 for conveying, positioning and releasing the central valved body 72, this ensures both the stability of the positioning of the annular support structure 60 throughout the entire implantation procedure of the prosthetic system and the precise spatial referencing between the various components 60 and 72 of the prosthetic system 70 at the time of the final release of the central valved body.

The example described above demonstrates how a device for deploying guide structures for interventional procedures within cardiac chambers, according to the embodiments of the invention, permits the fast, safe and effective execution of transcatheter or low-invasiveness procedures applied to anatomical structures of the heart.

The invention claimed is:

1. An annular support prosthetic system for heart valve replacement comprising:
    said annular support prosthetic system designed for deployment by one or more guide wires within a cardiac chamber utilizing an introducer catheter having at least a first main through lumen and at least a second through lumen;

said introducer catheter having the first main through lumen designed to be placed with at least two first guide catheters having respective deflected or deflectable distal ends that are adapted to emerge from the distal end of the introducer catheter to convey and direct the distal ends of respective one or more guide wires placed within the guide catheters towards a capture member of a capture system which is provided within the second through lumen of the introducer catheter and can be selectively drawn out of and retracted into the interior thereof;

the capture member being provided with a distal gripper for capturing the distal ends of the one or more guide wires and drawing the one or more guide wires into the introducer catheter;

wherein the second through lumen comprises a rectilinear portion and a curvature with respect to the axis of advance of the first main through lumen, and terminates in a distal orifice located on the lateral surface of the introducer catheter.

2. A prosthetic system for heart valve replacement according to claim 1, wherein each of the first guide catheters has characteristics of torsional rigidity.

3. A prosthetic system for heart valve replacement according to claim 1, wherein each of the first guide catheters accommodates and guides internally a respective second guide catheter having a torsionally rigid distal portion which is deflected or deflectable and is adapted to emerge from the distal end of the respective first guide catheter so as to guide and direct the distal end of the respective one or more guide wires.

4. A prosthetic system for heart valve replacement according to claim 3, further comprising a controlled deflection mechanism for one or more of the second guide catheters.

5. A prosthetic system for heart valve replacement according to claim 1, wherein the gripper of the capture member emerges selectively in a position spaced apart from the distal end of the introducer catheter.

6. A prosthetic system for heart valve replacement according to claim 1, wherein the gripper of the capture member comprises an automatically expanding collapsible structure retained selectively in a collapsed configuration by a retractable control sheath.

7. A prosthetic system for heart valve replacement according to claim 6, wherein the collapsible structure comprises a plurality of mesh elements which in the expanded configuration are adapted to trap the ends of the one or more guide wires without creating resistance to the blood flow.

8. A method for implantation of a prosthetic system to replace a heart valve, comprising the steps:

providing a multiple component annular support structure that is designed to be coupled together resulting in a single annular support structure, to be implanted with a valved prosthetic body within a mitral valve body;

positioning an introducer catheter with a distal end thereof close to the area of implantation of the prosthetic system;

advancing first guide catheters along the axis of the introducer catheter to a desired position, said first guide catheters having a deflected distal portion;

orientating the deflected distal portion of the first guide catheters in opposite directions lying substantially on the same plane;

causing the ends of corresponding guide wires to emerge from the inside of the first guide catheters;

drawing out a capture member having one or more grippers;

preparing said one or more grippers for capturing the ends of the guide wires;

directing the ends of the guide wires towards the one or more grippers;

capturing the guide wires with the one or more grippers and then drawing the guide wires into the introducer catheter by retracting the capture member; and inserting the multiple component annular support structure over the guide wires.

9. A method according to claim 8, wherein the method comprises the further step of advancing second guide catheters to move respective distal ends thereof out of the deflected distal portion of the first guide catheters and guiding the second guide catheters so as to position the second guide catheters substantially in the proximity of the drawn-out capture member, in order to direct the distal ends of the respective guide wires towards the capture member.

10. A prosthetic system for heart valve replacement, comprising:

a multiple component annular support structure within which a prosthetic valved body can be expanded until the valved body meets opposition;

the annular support structure being provided in two or more ring segments having a terminal connector;

wherein the two or more ring segments are interconnected by a connection system comprising pins adapted to engage in corresponding holes; and wherein solely engagement of the pins into the holes withstands the opposition exerted by the prosthetic valved body, and engagement of the pins into the holes results in the annular support structure that is stable, durable, and continuous.

11. A prosthetic system according to claim 10, wherein there are two ring segments and each end of one of the two ring segments is provided with the pins and each opposing end of the other one of the two ring segments is provided with the hole designed to receive the pins of the other one of the two ring segments.

12. A prosthetic system according to claim 10, wherein the two or more ring segments are deformable to provide a smaller overall radial dimension, adapted to allow the insertion of the segments by a catheter for conveyance thereof towards a heart valve implantation site.

13. A prosthetic system according to claim 10, wherein each of the two or more ring segments can be inserted separately into a cardiac chamber, where the terminal connector provides annular structural continuity after positioning of the segments.

14. A prosthetic system according to claim 10, wherein the annular support structure formed by connection of the two or more ring segments has predetermined shapes and dimensions, substantially coinciding with the anatomy of the annulus of the heart valve, so as to be capable of surrounding the valve in a continuous manner.

15. A prosthetic system according to claim 10, wherein each of the two or more ring segments is suitable for being supported by arms of a corresponding positioning and support device.

16. A prosthetic system according to claim 10, wherein each of the two or more ring segments is internally hollow to allow the passage of at least one guide wire.

17. A prosthetic system according to claim 16, wherein each of the two or more ring segments is an elongate tubular structure, bendable into two substantially identical portions, an aperture being provided in the vicinity of the halfway point of the elongate tubular structure, substantially in the area of bending of the ring segments, for the emergence of the at least one guide wire.

18. A prosthetic system according to claim 16, wherein the at least one guide wire comprises a plurality of guide wires that each emerge from the ends of each of the two or more ring segments, substantially at the positions of the terminal connector.

19. A method for implanting a prosthetic system for heart valve replacement comprising positioning the guide wires using the annular support prosthetic system according to claim 1, inserting and positioning ring segments, separately, around the native heart valve, providing annular structural continuity using a connector present on the segments, so as to surround the native heart valve, and expanding a prosthetic valved body within the native heart valve until the prosthetic valved body is opposed by the annular support prosthetic system, in such a way that leaflets of the native heart valve are secured between the ring segments.

* * * * *